United States Patent [19]

Lalk et al.

[11] 4,376,861

[45] Mar. 15, 1983

[54] METHOD FOR PREPARING 2-ALKENYL-2-OXAZOLINES

[75] Inventors: James W. Lalk, Shepherd; Gerald C. Kolb, Bay City; Donald A. Tomalia; Peter W. Owen, both of Midland, all of Mich.

[73] Assignee: The Dow Chemical Company, Midland, Mich.

[21] Appl. No.: 327,299

[22] Filed: Dec. 3, 1981

Related U.S. Application Data

[63] Continuation of Ser. No. 169,587, Jul. 17, 1980, abandoned, which is a continuation of Ser. No. 699,091, Jun. 23, 1976, abandoned.

[51] Int. Cl.$^3$ .................. C07D 263/12; C07D 263/14
[52] U.S. Cl. ..................................... 548/237; 548/239
[58] Field of Search ............................... 548/239, 237

[56] References Cited

FOREIGN PATENT DOCUMENTS 1385727  1/1965  France .
1557954  2/1969  France .

OTHER PUBLICATIONS

Seeliger et al., Angew. Chem. Int. Ed., vol. 5, No. 10, pp. 875, 882–883, (1966).

Primary Examiner—Paul M. Coughlan, Jr.
Attorney, Agent, or Firm—Charles J. Enright

[57] ABSTRACT

The process comprises the steps of:
  (A) reacting by contacting an anhydrous or substantially anhydrous 2-alkyl-2-oxazoline with formaldehyde in a molar ratio of at least about 1.5 moles of 2-alkyl-2-oxazoline per mole of formaldehyde, thereby forming 2-(α-hydroxymethylalkyl)-2-oxazoline,
  (B) recovering the 2-(α-hydroxymethylalkyl)-2-oxazoline from the reaction product of step (A), and
  (C) reacting by contacting the 2-(α-hydroxymethylalkyl)-2-oxazoline and step B with an alkali or alkaline earth metal hydroxide, thereby forming 2-alkenyl-2-oxazoline.

As an example, step A was conducted by reacting 2-ethyl-2-oxazoline (4 moles) having less than 1,000 ppm of water with paraformaldehyde (1 mole) at a reaction temperature of 100° C. for approximately 5.5 hours. The excess oxazoline reactant was removed along with water as "overheads" by fractional distillation of the reaction product, leaving the 2-(α-hydroxymethylethyl)-2-oxazoline in approximately 96 percent yield. Step C was then conducted by continuously adding the 2-(α-hydroxymethylethyl)-2-oxazoline to a stirred solution of sodium hydroxide in the mono-methyl ether of triethylene glycol at a temperature of from 100°–105° C. Under these conditions, the 2-isopropenyl-2-oxazoline and water were volatilized and recovered from the overheads. The product yield was approximately 98 percent of theory.

26 Claims, No Drawings

METHOD FOR PREPARING 2-ALKENYL-2-OXAZOLINES

CROSS-REFERENCE TO RELATED APPLICATION

This is a continuation of application Ser. No. 169,587, filed 7/17/80 which is a continuation of Ser. No. 699,091 filed 6/23/76 now abandoned.

BACKGROUND OF THE INVENTION

1. Field of the Invention:

This is a novel process which produces 2-(α-hydroxymethylalkyl)-2-oxazolines and 2-alkenyl-2-oxazolines in high yields.

2. Prior Art:

The 2-substituted-2-oxazolines form a known class of compounds. The literature is replete with information regarding methods of preparation and use of such compounds. See, for example, the following review articles: (a) Wiley et al., Chemical Reviews, Vol. 44, 447 (1949); (b) Seeliger et al., Angew. Chem. Internat. Edit., Vol. 5, No. 10 (1966); and (c) Frump, Chemical Reviews, 71, No. 5 (1971). See also the patents classified by the U.S. Patent and Trademark Office under 260/307F.

The 2-alkenyl-2-oxazolines are particularly useful compounds due to their difunctionality. Of these, the 2-vinyl- and 2-isopropenyl-2-oxazolines are perhaps two of the more useful compounds due to their reactivity in vinyl polymerizations. 2-Isopropenyl-2-oxazoline, for instance has a reactivity much like an acrylate in vinyl polymerizations.

Prior art methods of preparing 2-alkenyl-2-oxazolines have heretofore utilized relatively expensive reagents in multistep processes and the product yield was normally low. See, for example, the processes described in the above review articles and refer to the following U.S. Patents Nos.: 2,831,858; 2,968,657; 3,248,397; 3,466,308; 3,505,297; 3,523,123; 3,535,332; 3,661,922; 3,678,065; 3,839,350; French Pat. No. 1,557,954 and German Offen. No. 2,302,168.

The teachings of U.S. Pat. Nos. 3,535,332, 3,661,922, 3,839,350 and French Pat. No. 1,557,954 are of particular interest relative to the instant process. Each of these references teach that 2-hydroxyalkyl-2-oxazolines can be prepared by reacting a 2-alkyl-2-oxazoline with formaldehyde and that such compounds can be subsequently dehydrated to form the 2-alkenyl-2-oxazolines. In these reactions, the 2-hydroxyalkyl-2-oxazolines were prepared by reacting a 2-alkyl-2-oxazoline with an excess of formaldehyde even though the broad teachings indicated that equimolar amounts of reactants could be used. The disclosure in U.S. Pat. No. 3,523,123 is similar in this regard. The dehydration of the 2-hydroxyalkyl-2-oxazolines was thermally and/or catalytically induced. French Pat. No. 1,557,954 is the only reference which in fact shows the preparation of 2-isopropenyl-2-oxazoline; a compound which (along with 2-vinyl-2-oxazoline) is unique among other 2-alkenyl-2-oxazolines due to its extremely high reactivity.

SUMMARY OF THE INVENTION

We have now discovered a new method for preparing 2-alkenyl-2-oxazolines. The novel process comprises the steps of:

(A) reacting by contacting an anhydrous or substantially anhydrous 2-alkyl-2-oxazoline with formaldehyde in a molar ratio of at least about 1.5 moles of 2-alkyl-2-oxazoline per mole of formaldehyde, thereby forming the 2-(α-hydroxymethylalkyl)-2-oxazoline, (B) recovering the 2-(α-hydroxymethylalkyl)-2-oxazoline from the reaction product of step A, and (C) reacting by contacting the 2-(α-hydroxymethylalkyl)-2-oxazoline from step B with an alkali or alkaline earth metal hydroxide, thereby forming the 2-alkenyl-2-oxazoline.

Steps A and C individually as well as the combination of steps A-C are thought to be novel processes.

DETAILED DESCRIPTION OF THE INVENTION

Step A

Step A is conducted by reacting an anhydrous or essentially anhydrous 2-alkyl-2-oxazoline with formaldehyde to thus make the corresponding 2-(α-hydroxymethylalkyl)-2-oxazoline.

The 2-alkyl-2-oxazolines form a known class of compounds having many members, any member of which can be used herein so long as the 2-alkyl groups bear replaceable hydrogen on the α-carbon atom (i.e. adjacent to the oxazoline ring). The oxazoline reactants can bear inert ring substituents (e.g. alkyl groups) in the 4- and/or 5-ring positions. Preferred reactants correspond to the formula

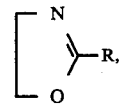

wherein R is an alkyl (preferably linear) group of from 1 to about 18 carbon atoms. The most preferred reactants are 2-methyl-2-oxazoline and 2-ethyl-2-oxazoline since these are the reactants leading to 2-vinyl-2-oxazoline and 2-isopropenyl-2-oxazoline, respectively. Other examples of suitable oxazoline reactants include: 2-propyl-, 2-butyl-, 2-hexyl-, 2-heptyl-, 2-nonyl-, 2-undecyl-, 2-heptadecyl-2-oxazoline and the corresponding 2-substituted 4-methyl-2-oxazolines, 4-ethyl-2-oxazolines, 4-butyl-2-oxazolines, 4,4-dimethyl-2-oxazolines, 4,5-dimethyl-2-oxazolines, and the like.

The yield of the desired 2-(α-hydroxymethyl)-2-oxazoline product is maximized when excess 2-alkyl-2-oxazoline is used in the process. Normally, we use at least about 1.5 moles of 2-alkyl-2-oxazoline per mole of formaldehyde. The preferred ratio of reactants, however, is from about 2 to about 10 moles of oxazoline reactant to formaldehyde and the most preferred ratio is from about 3 to about 5 moles of oxazoline reactant per mole of formaldehyde.

In addition to the utilization of excess oxazoline reactant in the process, we have found that product yields are maximized by conducting the reaction under anhydrous or substantially anhydrous conditions. For this reason, we prefer to predry the oxazoline reactant (normally with molecular sieves or solid sodium hydroxide) and use a source of formaldehyde that is low in water content. Paraformaldehyde having a 95 percent or greater formaldehyde content is commercially available and is the formaldehyde source of choice. Formaldehyde per se and other non-aqueous sources of formaldehyde (e.g. trioxane and other polymers of formaldehyde) are suitable, however.

The process may be conducted at any suitable temperature that promotes the reaction and is below the decomposition temperature of the desired product. Satisfactory reaction rates have been observed at temperatures of from about 90° to about 115° C. and temperatures of from about 95° to about 105° C. are normally preferred; at these temperatures, reaction times of from about 2 to about 8 hours are conventional. Inert organic solvents (e.g., benzene, toluene, etc.) may be used if desired but we prefer to conduct the process neat.

Step B:

The 2-($\alpha$-hydroxymethylalkyl)-2-oxazoline may be recovered from the reaction product of Step A by any of several conventional techniques. E.g., solvent extraction, fractional distillation, etc. In those instances where the oxazoline reactant and product are liquids and/or low melting solids, Fractional distillation under reduced pressure at a temperature below the decomposition temperature of 2-($\alpha$-hydroxymethylalkyl)-2-oxazoline is normally used. In this manner, the excess oxazoline reactant and water normally co-distill and are recovered. The reactant oxazoline/water distillate can then be dried and the 2-alkyl-2-oxazoline recycled back into step A. The 2-($\alpha$-hydroxymethyalkyl)-2-oxazolines are higher boiling and thus recovering from the distillation as the "pot residues" which can be used per se in Step C but are preferably further purified (generally by distillation using a falling film still or other conventional techniques) before use.

We have found that the overall yield of the 2-alkenyl-2-oxazoline is maximized when step B is conducted as soon as practical after step A.

Step C

In this step, the 2-($\alpha$-hydroxymethylalkyl)-2-oxazoline is dehydrated by contacting same with an alkali or alkaline earth metal hydroxide, thereby forming the 2-alkenyl-2-oxazoline. This reaction may be conducted at any temperature sufficient to promote the dehydration but we have found satisfactory reaction rates normally occur at temperatures of from about 95° to about 200° C. under reduced pressure (e.g., from about 10 to about 150 mm Hg).

Essentially any alkali or alkaline earth metal hydroxide can be used in Step C but the efficiency of the alkali or alkaline earth metal hydroxides to promote the dehydration tends to correlate with the degree of solubility of the alkali or alkaline earth metal hydroxide in hot water. That is, the more water soluble the alkali or alkaline earth metal hydroxide is in hot water the more efficient it appears to be in dehydrating the 2-($\alpha$-hydroxymethylalkyl)-2-oxazoline. Lithium hydroxide, sodium hydroxide, potassium hydroxide and barium hydroxide are the preferred catalysts and sodium hydroxide is most preferred, based upon its efficiency and relative cost.

Step C may be conducted in a batchwise or continuous manner and we prefer to conduct it in a continuous manner. In the continuous process, the 2-($\alpha$-hydroxymethyl-alkyl)-2-oxazoline is added to the alkali or alkaline earth metal hydroxide catalyst at reaction temperature. The 2-alkenyl-2-oxazoline can normally be volatilized at the reaction temperatures under reduced pressure and is co-distilled with water from the reaction vessel. Thus, the 2-($\alpha$-hydroxymethylalkyl)-2-oxazoline is metered into the reaction vessels at substantially the same rate at which the 2-alkenyl-2-oxazoline/water mixture is removed as overheads. The 2-alkenyl-2-oxazoline can be conveniently recovered from the 2-alkenyl-2-oxazoline/-water solution using conventional solvent extraction techniques.

Inert organic solvents which remain liquid at the reaction temperature may be included in step C if desired. However, we find that step C is preferably conducted either neat or in the presence of a lower alkyl monoether of a polyalkylene glycol. The latter compounds are known to be solvents for the alkali and alkaline earth metal hydroxides and are, therefore, preferred organic solvents for use in this step. This known class of compounds include, for example, the methyl, ethyl, propyl and butyl ethers of diethylene glycol, triethylene glycol, etc. The monomethyl other of triethylene glycol appears to be the most efficient when sodium hydroxide is used as the catalyst.

The following examples will further illustrate the invention.

EXAMPLE 1

Preparation of 2-Isopropenyl-2-oxazoline

2-Ethyl-2-oxazoline (594 g; 6.0 moles) and 95 percent paraformaldehyde (63.2 g; 2.0 moles) were charged to a reaction vessel equipped with a mechanical stirrer and condenser. The reaction mixture was heated to 100° C. with stirring and maintained under these conditions for 4 hours. A sample of the reaction mixture was then analyzed by vapor phase chromatography with the following results: 60.7 weight percent 2-ethyl-2-oxazoline; 37.9 weight percent 2-($\alpha$-hydroxymethylethyl)-2-oxazoline; and the remaining 1.4 weight percent was not identified. On this data, the conversion of 2-ethyl-2-oxazoline was 98.5 percent and the percent yield of 2-($\alpha$-hydroxymethylethyl)-2-oxazoline was 96.5 percent. The excess 2-ethyl-2-oxazoline was removed from the reaction mixture by distillation under reduced pressure leaving the desired 2-($\alpha$-hydroxymethylethyl)-2-oxazoline as the "still bottoms".

Sodium hydroxide beads (60.0 g; 1.5 mole) were added to a reaction vessel equipped with a mechanical stirrer, a dropping funnel and a distillation column packed with ¼ inch glass beads. This material was heated to a pot temperature of approximately 175° C. at a pressure of 150 mm Hg. To this heated system was added the 2-($\alpha$-hydroxymethylethyl)-2-oxazoline from the above (containing 100 ppm of a polymerization inhibitor) at a rate of approximately 1 g per minute. All volatiles passing through the distillation column were collected in a cold trap and analyzed by vapor phase chromatography using 1,2,4-trichlorobenzene as an internal standard. The mixture contained 2.5 weight percent unreacted 2-ethyl-2-oxazoline; 11.7 weight percent water; and 85.8 weight percent 2-isopropenyl-2-oxazoline. This amounts to a 97.8 percent yield of 2-isopropenyl-2-oxazoline.

Similar high yields were obtained when the dehydration was conducted using sodium hydroxide dissolved in monomethyl ether of triethylene glycol and a minor amount of water. Data obtained on a series of such dehydrations indicate that the effective life of the sodium hydroxide catalyst was extended by using this material as a reaction medium.

The crude aqueous 2-isopropenyl-2-oxazoline produced by the above technique is surprisingly useful in making 2-aminoethyl methacrylate salts by the process described in the application submitted even date herewith by Lalk et al. entitled "Process for Preparing 2-Aminoethyl Methacrylate Salts", Ser. No. 699119 filed 6/23/76 now abandoned (the disclosure of which is herewith incorporated by reference).

EXAMPLE 2

Preparation of 2-(α-dodecenyl)-2-oxazoline

Using the same ratio of reactants and substantially the same process conditions, 2-lauryl-2-oxazoline was reacted with paraformaldehyde at 100° C. for 5 hours. The 2-(α-hydroxymethylalkyl)-2-oxazoline product crystallized out of the liquid reaction mixture. The solid product was separated by filtration and recrystallized in n-hexane. The recrystallized product was obtained as a white crystalline solid melting at 64°–67° C. The yield of recrystallized product was 70 percent, based on formaldehyde. A portion of this recrystallized material (15 g; 0.06 mole) was warmed to a melt and added dropwise to sodium hydroxide beads (20 g) preheated to a temperature of 175° C. at 0.5 mm Hg. The 2-(α-dodecenyl)-2-oxazoline was, of course, immediately volatilized and was collected in a cold trap cooled with ice water. The product was thus obtained as a liquid boiling at 127° C. at 0.03 mm Hg in 71 percent yield, based on the starting 2-(α-hydroxymethyllauryl)-2-oxazoline.

EXAMPLE 3

Preparation of 2-Vinyl-2-oxazoline

Using the same reaction conditions set forth in Example 1, 2-methyl-2-oxazoline was reacted wtih formaldehyde, thereby forming 2-hydroxyethyl-2-oxazoline in approximately 83 percent distilled yield. The product had a boiling point of 55°–58° C. at 0.5 mm Hg. Dehydration of the product was likewise performed under conditions similar to Example 1. Sodium hydroxide beads (20 g) were heated to 150° C. at 150 mm Hg. To this was added dropwise the 2-hydroxyethyl-2-oxazoline (56 g; 0.49 mole) and the volatiles thus formed collected in a receiver cooled with ice water. The condensed volatiles were identified as an aqueous solution of 2-vinyl-2-oxazoline which boiled at 83°–85° C. at 150 mm Hg. No impurities appeared to be present in the aqueous solution of the 2-vinyl-2-oxazoline and the recovered product amounted to a material balance of over 95 percent.

EXAMPLE 4

Preparation of 2-Isopropenyl-2-oxazoline

A stainless steel reaction vessel was loaded with paraformaldehyde (96.7 percent) and 2-ethyl-2-oxazoline in a molar ratio of approximately 4 moles of oxazoline per mole of formaldehyde. The oxazoline reactant was predried over 3 A molecular sieves and contained only 490 ppm water. The reaction mixture was blanketed with dry nitrogen and the system closed. The reaction mixture was heated to 100° C. and maintained at this temperature for a period of 4.5 hours. The excess 2-ethyl-2-oxazoline was subsequently distilled from the reaction mixture at 20 mm Hg pressure. The distillation took two hours and was terminated when the overhead temperature reached 97° C. This gave 30 parts by weight of pot residue containing 92 weight percent 2-(α-hydroxymethylethyl)-2-oxazoline and 74.5 parts by weight of distillate containing 98 weight percent 2-ethyl-2-oxazoline, 1.5 weight percent 2-(α-hydroxymethylethyl)-2-oxazoline, 0.52 weight percent water, and a trace of 2-isopropenyl-2-oxazoline. About 1.2 parts by weight of the reaction mixture was removed during the course of reaction as samples. The yield of 2-(α-hydroxymethylethyl)-2-oxazoline was thus 94 percent, based on formaldehyde charged and 92 percent based on 2-ethyl-2-oxazoline consumed.

The crude 2-(α-hydroxymethylethyl)-2-oxazoline was flash distilled in a continuous distillation in which an aliquot of the crude material was heated to distillation temperature and thereafter the crude material was added at essentially the same rate at which the distillate was taken overhead. The overhead temperature was 87°–97° C./2.6–5 mm Hg.

Sodium hydroxide beads (43.9 parts by weight) and water (28.9 parts by weight) were charged to a reaction vessel containing a mechanical stirrer, heating means, and distillation. The mixture was stirred until the sodium hydroxide dissolved after which the monomethyl ether of triethylene glycol (150.6 parts by weight) was added. Pressure over the system was reduced to 40 mm Hg and the mixture heated to 97° C. causing some of the water to distill overhead at approximately 36° C. and leaving a solution of the sodium hydroxide in the pot. The distilled 2(α-hydroxymethylethyl)-2-oxazoline was then added to the reaction flask at a controlled rate by means of a Milton Roy ® metering pump. During this addition, 2-isopropenyl-2-oxazoline and water were formed which were simultaneously removed overhead during the reaction at a head temperature of 56°–59° C. and a pot temperature of from 102°–108° C./39–40 mm Hg. After the addition of the 2-(α-hydroxymethylethyl)-2-oxazoline was complete, the pot temperature was raised to 150° C. over a twenty minute period to drive out the last of the available 2-isopropenyl-2-oxazoline. The water-white clear distillate was anlayzed by vapor phase chromatography using 1,2,4-trichlorobenzene as an internal standard. This analysis showed the distillate to be 83.9 weight percent 2-isopropenyl-2-oxazoline, 15.6 weight percent water (by Karl Fischer analysis) and 0.28 weight percent 2-ethyl-2-oxazoline. This represents a 97.1 percent yield of 2-isopropenyl-2-oxazline based on the 2-(α-hydroxymethylethyl)-2-oxazoline charged.

The products in the above reactions were also identified by infrared and nuclear magnetic resonance spectroscopy.

Other 2-alkenyl-2-oxazolines could be similarly prepared using the appropriate 2-alkyl-2-oxazoline and formaldehyde reactants as set forth in the specification above.

We claim:
1. A method for preparing a 2-alkenyl-2-oxazoline comprising the steps of:
   (A) reacting by contacting an anhydrous or substantially anhydrous 2-alkyl-2-oxazoline or inertly-substituted 2-alkyl-2-oxazoline with formaldehyde in a molar ratio of at least about 3 moles of 2-alkyl-2-oxazoline per mole of formaldehyde, thereby forming the corresponding 2-(α-hydroxymethylalkyl)-2-oxazoline,
   (B) recovering the 2-(α-hydroxymethylalkyl)-2-oxazoline from the reaction product of step A, and
   (C) reacting by contacting the 2(α-hydroxymethylalkyl)-2-oxazoline from step B with potassium or sodium hydroxide, thereby forming the 2-alkenyl-2-oxazoline.

2. The process defined by claim 1 wherein said 2-alkyl-2-oxazoline corresponds to the formula:

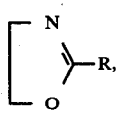

wherein R is alkyl or inertly-substituted alkyl of from 1 to about 18 carbon atoms having replaceable hydrogen on the α-carbon atom.

3. The process defined by claim 2 wherein R is a linear alkyl group.

4. The process defined by claim 3 wherein R is methyl or ethyl.

5. The process defined by claim 1 wherein the molar ratio of oxazoline to formaldehyde is from about 3 to about 10.

6. The process defined by claim 5 wherein the molar ratio is from about 3 to about 5.

7. The process defined by claim 1 wherein the reaction temperature in step A is from about 90° to about 115° C.

8. The process defined by claim 7 wherein the reaction temperature of step A is from about 95° to about 105° C.

9. The process defined by claim 1 wherein the reaction temperature of step C is from about 95° to about 200° C.

10. The process defined by claim 9 wherein sodium hydroxide is employed in step C.

11. The process defined by claim 10 wherein step C is conducted neat or in the presence of a lower alkyl monoether of a polyalkylene glycol.

12. The process defined by claim 10 wherein said lower alkyl monoether of a polyalkylene glycol is the monomethyl ether of triethylene glycol.

13. The process defined by claim 1 comprising the steps of:
    (A) reacting by contacting anhydrous or substantially anhydrous 2-ethyl-2-oxazoline with paraformaldehyde, having a formaldehyde content of at least about 95 weight percent, in a molar ratio of from about 3 to about 5 moles of 2-ethyl-2-oxazoline per mole of formaldehyde at a reaction temperature of from about 95° to about 105° C., thereby forming 2-(α-hydroxymethylethyl)-2-oxazoline,
    (B) recovering the 2-(α-hydroxymethylethyl)-2-oxazoline from the reaction product of step A by fractional distillation,
    (C) reacting by contacting the 2-(α-hydroxymethylethyl)-2-oxazoline from step B with sodium hydroxide dissolved in an aqueous solution of the monomethyl ether of triethylene glycol at a reaction temperature of from about 100° to about 105° C. under reduced pressure, thereby forming 2-isopropenyl-2-oxazoline and water which are co-distilled from the reaction mixture essentially as they are formed, and
    (D) recovering the 2-isopropenyl-2-oxazoline from step C as an aqueous solution thereof by condensing the distillate vapors.

14. The process defined by claim 1 wherein step C is conducted at a temperature and pressure such that the 2-alkenyl-2-oxazoline product and water are co-distilled from the reaction mixture.

15. The process defined by claim 14 wherein said 2-alkyl-2-oxazoline is 2-methyl-2-oxazoline or 2-ethyl-2-oxazoline.

16. The process defined by claim 15 wherein said 2-alkyl-2-oxazoline is 2-ethyl-2-oxazoline.

17. The process defined by claim 4 wherein R is ethyl.

18. A method of preparing a 2-(α-hydroxymethylalkyl)-2-oxazoline comprising reacting by contacting an anhydrous or substantially anhydrous 2-alkyl-2-oxazoline with formaldehyde in a molar ratio of at least about 3 moles of 2-alkyl-2-oxazoline per mole of formaldehyde.

19. The process defined by claim 18 wherein said 2-alkyl-2-oxazoline corresponds to the formula:

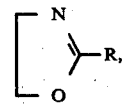

wherein R is alkyl or inertly-substituted alkyl of from 1 to about 18 carbon atoms having replaceable hydrogen on the α-carbon atom.

20. The process defined by claim 19 wherein R is a linear alkyl group.

21. The process defined by claim 20 wherein R is methyl or ethyl.

22. The process defined by claim 18 wherein the molar ratio of oxazoline to formaldehyde is from about 3 to about 10.

23. The process defined by claim 22 wherein the molar ratio is from about 3 to about 5.

24. The process defined by claim 18 wherein the reaction temperature is from about 90° C. to about 115° C.

25. The process defined by claim 24 wherein the reaction temperature is from about 95° C. to about 105° C.

26. The process defined by claim 25 wherein said 2-alkyl-2-oxazoline is 2-ethyl-2-oxazoline and the molar ratio of oxazoline to formaldehyde is from about 3 to about 5.

* * * * *

UNITED STATES PATENT AND TRADEMARK OFFICE
CERTIFICATE OF CORRECTION

PATENT NO. : 4,376,861

DATED : March 15, 1983

INVENTOR(S) : James W. Lalk, Gerald C. Kolb, Donald A. Tomalia and Peter W. Owen It is certified that error appears in the above—identified patent and that said. Letters Patent is hereby corrected as shown below:

Title page, Abstract, line 12, "oxazoline and step B" should read -- oxazoline from step B --.

Column 1, line 23, "Reviews, 71," should read -- Reviews, Vol. 71, --.

Column 3, line 18, "solids, Fractional" should read -- solids, fractional --.

Column 3, line 26, "thus recovering from" should read -- thus recovered from --.

Column 4, line 15, "monomethyl other of" should read -- monomethyl ether of --.

Column 5, line 32, "reacted wtih formalde-" should read -- reacted with formalde- --.

Column 5, line 55, "3 A molecular" should read -- 3 $\overset{o}{A}$ molecular --.

Column 6, line 36, "was anlayzed" should read -- was analyzed --.

Column 6, line 65, "the 2(α-hydroxymethylalkyl)" should read -- the 2-(α-hydroxymethylalkyl) --.

UNITED STATES PATENT AND TRADEMARK OFFICE
CERTIFICATE OF CORRECTION

PATENT NO. : 4,376,861

DATED : March 15, 1983

INVENTOR(S) : James W. Lalk, Gerald C. Kolb, Donald A. Tomalia and Peter W. Owen It is certified that error appears in the above—identified patent and that said Letters Patent is hereby corrected as shown below:

Column 6, line 43, "oxazline based on" should read -- oxazoline based on --.

Signed and Sealed this

Second Day of August 1983

[SEAL]

Attest:

GERALD J. MOSSINGHOFF

Attesting Officer

Commissioner of Patents and Trademarks